(12) United States Patent
Koseoglu et al.

(10) Patent No.: US 10,345,285 B2
(45) Date of Patent: *Jul. 9, 2019

(54) CHARACTERIZATION OF AN AROMATICITY VALUE OF CRUDE OIL BY ULTRAVIOLET VISIBLE SPECTROSCOPY

(71) Applicant: Saudi Arabian Oil Company, Dhahran (SA)

(72) Inventors: Omer Refa Koseoglu, Dhahran (SA); Adnan Al-Hajji, Dhahran (SA); Gordon Jamieson, London (GB)

(73) Assignee: Saudi Arabian Oil Company, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 15/266,268

(22) Filed: Sep. 15, 2016

(65) Prior Publication Data

US 2017/0003217 A1  Jan. 5, 2017

Related U.S. Application Data

(63) Continuation of application No. 15/235,680, filed on Aug. 12, 2016, now Pat. No. 10,031,121, which is a continuation-in-part of application No. PCT/US2016/012114, filed on Jan. 5, 2016, and a
(Continued)

(51) Int. Cl.
*B01D 15/08* (2006.01)
*G01N 33/28* (2006.01)
*G01N 21/33* (2006.01)
*G01N 1/38* (2006.01)

(52) U.S. Cl.
CPC .......... *G01N 33/2823* (2013.01); *G01N 1/38* (2013.01); *G01N 21/33* (2013.01); *G01N 2201/061* (2013.01)

(58) Field of Classification Search
USPC ...................................... 210/198.2
See application file for complete search history.

(56) References Cited

U.S. PATENT DOCUMENTS

| 4,251,870 A | 2/1981 | Jaffe |
| 4,971,915 A | 11/1990 | Schwartz et al. |

(Continued)

FOREIGN PATENT DOCUMENTS

| CA | 2781273 A1 | 12/2013 |
| EP | 0305090 A2 | 8/1988 |

(Continued)

OTHER PUBLICATIONS

Birch, C., Oil & Gas Journal, Jan. 14, 2002, pp. 54-59.
(Continued)

*Primary Examiner* — Lam S Nguyen
(74) *Attorney, Agent, or Firm* — Abelman, Frayne & Schwab

(57) ABSTRACT

A system and a method for characterizing an aromaticity value of a crude oil sample from the weight and ultraviolet visible spectroscopy of the sample id provided. The system and method includes calculating and assigning a crude oil ultraviolet visible index and using the assigned index to calculate and assign an aromaticity value of the sample, and optionally to calculate and assign an API gravity.

53 Claims, 3 Drawing Sheets

Related U.S. Application Data continuation-in-part of application No. 13/400,787, filed on Feb. 21, 2012, now Pat. No. 9,778,240.

(60) Provisional application No. 62/099,658, filed on Jan. 5, 2015, provisional application No. 61/445,217, filed on Feb. 22, 2011.

(56) References Cited

U.S. PATENT DOCUMENTS

| | | | |
|---|---|---|---|
| 4,988,446 A * | 1/1991 | Haberman | C10G 11/187 |
| | | | 210/198.2 |
| 5,223,714 A | 6/1993 | Maggard | |
| 5,452,232 A | 9/1995 | Espinosa et al. | |
| 5,490,085 A | 2/1996 | Lambert et al. | |
| 5,572,030 A | 11/1996 | Ranson et al. | |
| 5,600,134 A | 2/1997 | Ashe et al. | |
| 5,602,755 A | 2/1997 | Ashe et al. | |
| 5,656,810 A | 8/1997 | Alfano et al. | |
| 5,699,269 A | 12/1997 | Ashe et al. | |
| 6,258,987 B1 | 7/2001 | Schmidt et al. | |
| 6,602,403 B1 | 8/2003 | Steffens et al. | |
| 6,711,532 B1 | 3/2004 | Spieksma | |
| 6,841,779 B1 | 1/2005 | Roehner et al. | |
| 8,930,149 B1 | 1/2015 | Koseoglu | |
| 2002/0052769 A1 | 5/2002 | Navani et al. | |
| 2003/0141459 A1 | 7/2003 | Hegazi et al. | |
| 2003/0195708 A1 | 10/2003 | Brown | |
| 2007/0050154 A1 | 3/2007 | Albahri | |
| 2007/0231912 A1 | 10/2007 | Reischman et al. | |
| 2007/0295640 A1 | 12/2007 | Tan et al. | |
| 2008/0040051 A1 | 2/2008 | Franklin et al. | |
| 2008/0248967 A1 | 10/2008 | Butler et al. | |
| 2008/0260584 A1 | 10/2008 | Gudde et al. | |
| 2010/0113311 A1 | 5/2010 | Eggleston et al. | |
| 2010/0211329 A1 | 8/2010 | Farquharson et al. | |
| 2011/0152136 A1 | 6/2011 | Hughes et al. | |
| 2014/0075827 A1 | 3/2014 | Gonzalez et al. | |
| 2014/0156241 A1 | 6/2014 | Kumar et al. | |
| 2015/0106027 A1 | 4/2015 | Koseoglu et al. | |
| 2015/0106029 A1 | 4/2015 | Koseoglu et al. | |

FOREIGN PATENT DOCUMENTS

| | | |
|---|---|---|
| EP | 0304232 A2 | 2/1989 |
| EP | 0552300 A1 | 7/1993 |
| EP | 0794433 A1 | 9/1997 |
| EP | 0984277 A1 | 3/2000 |
| WO | 03/048759 A1 | 6/2003 |
| WO | 2004033513 A2 | 4/2004 |
| WO | 2006030218 A1 | 3/2006 |
| WO | 2009082418 A2 | 7/2009 |
| WO | 2013102916 A1 | 7/2013 |

OTHER PUBLICATIONS

Pavlovic, K., Oil & Gas Journal, Nov. 22, 1999, pp. 51-56.

Coen, Duvekot, Fast Analysis of Paraffins, iso-Paraffins, Olefins, iso-Olefins, Naphthenes and Aromatics in Hydrocarbon Streams, Varian, Inc., pp. 1-4.

ASTM D2887-01, Standard Test Method for Boiling Range Distribution of Petroleum Fractions by Gas Chromatography, Annual Book of ASTM Standards, vol. 14, No. 02, pp. 204-216.

Hidajat, K, et al., Quality characterisation of crude oils by partial least square calibration of NIR spectral profiles, Near Infrared Spectrosc, vol. 8, pp. 53-59.

Falla, F, et al., Characterization of crude petroleum by NIR, Journal of Petroleum Science and Engineering, vol. 51, 2006, pp. 127-137.

Terra, L. et al., Petroleomics by electrospray ionization FT-ICR mass spectrometry coupled to partial least squares with variable selection methods: prediction of the total acid number of crude oils, Analyst, vol. 139, 2014, pp. 4908-4916.

Pereira,Thieres M. C., An evaluation of the aromaticity of asphaltenes using atmospheric pressure photoionization Fourier transform ion cyclotron resonance mass spectrometry—APP (±) FT-ICR MS, Fuel, vol. 118, 2014, pp. 348-357.

Mckenna, Amy M., Heavy Petroleum Composition. 1. Exhaustive Compositional Analysis of Athabasca Bitumen HVGO Distillates by Fourier Transform Ion Cyclotron Resonance Mass Spectrometry: A Definitive Test of the Boduszynski Model, Energy Fuels, 24, 2010, pp. 2929-2038.

Yamashita, G.T., Evaluation of Integration Procedures for PNA Analysis by C-13 NMR, Symposium on Analytical Chemistry of Heavy OilslResids Presented Before the Division of Petroleum Chemistry, Inc., American Chemical Society, Dallas Meeting, Apr. 9-14, 1989, pp. 301-305.

Adhvaryu, A et al., Quantitative NMR Spectroscopy for the Prediction of Base Oil Properties, Tribology Transactions, vol. 43, No. 2, pp. 245-250.

Shea, T.M., Modeling Base Oil Properties using NMR Spectroscopy and Neural Networks, Tribology Transactions, vol. 16, No. 3, 2003, pp. 296-302.

Souza, C. et al., Cetane Number Assessment in Diesel Fuel by 1H or Hydrogen Nuclear Magnetic Resonance-Based Multivariate Calibration, Energy & Fuels, vol. 28, 2014, pp. 4958-4962.

Hasan, M.U. et al., Structural characterization of Saudi Arabian heavy crude oil by n.m.r. spectroscopy, Fuel, vol. 62, 1983, pp. 518-523.

Seetar, G, et al., Cetana Number Predictions of a Trial Index Based on Compositional Analysis, American Chemical Society, 1989, pp. 308-312.

Cookson, D.J. et al., Investigation of the Chemical Basis of Diesel Fuel Properties, Energy & Fuels, vol. 2, No. 6, 1988, pp. 854-860.

Patra, D, et al, Determination of Synchronous Fluorescence Scan Parameters for Certain Petroleum Products, Journal of Scientific & Industrial Research, Apr. 1, 2000, pp. 300-305.

Khanmohammadi, M, et al., Characterization of petroleum-based products by infrared spectroscopyu and chemometrics, Trac Trends in Analytical Chem, vol. 35, 2012.

Kok, M, et al., High pressure TGA analysis of crude oils, Thermochimica Acta., vol. 287, No. 1, Sep. 1, 1996, pp. 91-99.

PCT/US2016/012114, International Search Report and Written Opinion dated Jun. 7, 2016, 18 pages.

\* cited by examiner

CHARACTERIZATION OF AN AROMATICITY VALUE OF CRUDE OIL BY ULTRAVIOLET VISIBLE SPECTROSCOPY

RELATED APPLICATIONS

This application
is a continuation of U.S. patent application Ser. No. 15/235,680, which
is a continuation-in-part under 35 USC § 365(c) of PCT Patent Application No. PCT/US16/12114 filed Jan. 5, 2016, which claims the benefit of U.S. Provisional Patent Application No. 62/099,658 filed Jan. 5, 2015, and
is a continuation-in-part of U.S. patent application Ser. No. 13/400,787 filed Feb. 21, 2012, which claims the benefit of U.S. Provisional Patent Application No. 61/445,217 filed Feb. 22, 2011,
the disclosures of which are hereby incorporated by reference.

FIELD OF THE INVENTION

This invention relates to a method and process for the evaluation of samples of crude oil and its fractions by ultraviolet visible spectroscopy.

BACKGROUND OF THE INVENTION

Crude oil originates from the decomposition and transformation of aquatic, mainly marine, living organisms and/or land plants that became buried under successive layers of mud and silt some 15-500 million years ago. They are essentially very complex mixtures of many thousands of different hydrocarbons. Depending on the source, the oil predominantly contains various proportions of straight and branched-chain paraffins, cycloparaffins, and naphthenic, aromatic, and polynuclear aromatic hydrocarbons. These hydrocarbons can be gaseous, liquid, or solid under normal conditions of temperature and pressure, depending on the number and arrangement of carbon atoms in the molecules.

Crude oils vary widely in their physical and chemical properties from one geographical region to another and from field to field. Crude oils are usually classified into three groups according to the nature of the hydrocarbons they contain: paraffinic, naphthenic, asphaltic, and their mixtures. The differences are due to the different proportions of the various molecular types and sizes. One crude oil can contain mostly paraffins, another mostly naphthenes. Whether paraffinic or naphthenic, one can contain a large quantity of lighter hydrocarbons and be mobile or contain dissolved gases; another can consist mainly of heavier hydrocarbons and be highly viscous, with little or no dissolved gas. Crude oils can also include heteroatoms containing sulfur, nitrogen, nickel, vanadium and other elements in quantities that impact the refinery processing of the crude oil fractions. Light crude oils or condensates can contain sulfur in concentrations as low as 0.01 W %; in contrast, heavy crude oils can contain as much as 5-6 W %. Similarly, the nitrogen content of crude oils can range from 0.001-1.0 W %.

The nature of the crude oil governs, to a certain extent, the nature of the products that can be manufactured from it and their suitability for special applications. A naphthenic crude oil will be more suitable for the production of asphaltic bitumen, a paraffinic crude oil for wax. A naphthenic crude oil, and even more so an aromatic one, will yield lubricating oils with viscosities that are sensitive to temperature. However, with modern refining methods there is greater flexibility in the use of various crude oils to produce many desired type of products.

When produced at the well, crude oil is usually accompanied by variable amounts of sweet and sour gases, as well as formation brines having high total dissolved solids (TDS). The crude oil is usually stabilized and desalted soon after its production from a well.

A crude oil assay is a traditional method of determining the nature of crude oils for benchmarking purposes. Crude oils are subjected to true boiling point (TBP) distillations and fractionations to provide different boiling point fractions. The crude oil distillations are carried out using the American Standard Testing Association (ASTM) Method D 2892. The common fractions and their nominal boiling points are given in Table 1.

TABLE 1

| Fraction | Boiling Point, ° C. |
| --- | --- |
| Methane | −161.5 |
| Ethane | −88.6 |
| Propane | −42.1 |
| Butanes | −6.0 |
| Light Naphtha | 36-90 |
| Mid Naphtha | 90-160 |
| Heavy Naphtha | 160-205 |
| Light Gas Oil | 205-260 |
| Mid Gas Oil | 260-315 |
| Heavy Gas Oil | 315-370 |
| Light Vacuum Gas Oil | 370-430 |
| Mid Vacuum Gas Oil | 430-480 |
| Heavy Vacuum Gas Oil | 480-565 |
| Vacuum Residue | 565+ |

The yields, composition, physical and indicative properties of these crude oil fractions, where applicable, are then determined during the crude assay work-up calculations. Typical compositional and property information obtained in a crude oil assay is given in Table 2.

TABLE 2

| Property | Unit | Property Type | Fraction |
| --- | --- | --- | --- |
| Yield Weight and Volume % | W % | Yield | All |
| API Gravity | ° | Physical | All |
| Viscosity Kinematic @ 38° C. | ° | Physical | Fraction boiling >250° C. |
| Refractive Index @ 20° C. | Unitless | Physical | Fraction boiling <400° C. |
| Sulfur | W % | Composition | All |
| Mercaptan Sulfur, W % | W % | Composition | Fraction boiling <250° C. |
| Nickel | ppmw | Composition | Fraction boiling >400° C. |
| Nitrogen | ppmw | Composition | All |
| Flash Point, COC | ° C. | Indicative | All |
| Cloud Point | ° C. | Indicative | Fraction boiling >250° C. |
| Pour Point, (Upper) | ° C. | Indicative | Fraction boiling >250° C. |
| Freezing Point | ° C. | Indicative | Fraction boiling >250° C. |
| Microcarbon Residue | W % | Indicative | Fraction boiling >300° C. |
| Smoke Point, mm | mm | Indicative | Fraction boiling between 150-250 |
| Octane Number | Unitless | Indicative | Fraction boiling <250° C. |
| Cetane Index | Unitless | Indicative | Fraction boiling between 150-400 |
| Aniline Point | ° C. | Indicative | Fraction boiling <520° C. |

Due to the number of distillation cuts and the number of analyses involved, the crude oil assay work-up is both costly and time consuming.

In a typical refinery, crude oil is first fractionated in the atmospheric distillation column to separate sour gas and light hydrocarbons, including methane, ethane, propane, butanes and hydrogen sulfide, naphtha (36°-180° C.), kerosene (180°-240° C.), gas oil (240°-370° C.) and atmospheric residue (>370° C.). The atmospheric residue from the atmospheric distillation column is either used as fuel oil or sent to a vacuum distillation unit, depending on the configuration of the refinery. The principal products obtained from vacuum distillation are vacuum gas oil, comprising hydrocarbons boiling in the range 370°-520° C., and vacuum residue, comprising hydrocarbons boiling above 520° C. The crude assay data help refiners to understand the general composition of the crude oil fractions and properties so that the fractions can be processed most efficiently and effectively in an appropriate refining unit.

In the field of organic chemistry, UV-visible spectrophotometry, which deals with electronic transitions within molecules, has traditionally provided unique information about aromatic and heteroaromatic compounds which absorb strongly in the UV region (200 nm-400 nm). Despite this and owing to the complex molecular nature of crude oil, UV-visible spectra of these oils are often described as featureless, poorly defined spectra.

New rapid and direct methods to help better understand crude oil composition and properties from the analysis of whole crude oil will save producers, marketers, refiners and/or other crude oil users substantial expense, effort and time. Therefore, a need exists for an improved system and method for determining properties of crude oil fractions from different sources and classifying the crude oil fractions based on their boiling point characteristics and/or properties.

SUMMARY OF THE INVENTION

Systems and methods are provided for characterizing samples of crude oil based on an index derived from the UV visible spectra and gravity. The wavelength maxima of known aromatic compounds and components are evaluated and extracted from the UV spectra of crude oils, which can be used to formulate and assign indices for the aromatic content of the crude oil. Properties of the oil including API gravity, sulfur content, and other selected characteristics that define the quality and nature of the constituent products, are assigned as a function of these indices. Importantly, this information can be obtained relatively rapidly and inexpensively from a UV-visible scan as compared to conventional assay methods described above.

In the method and system herein, a crude oil ultraviolet visible index (which will be referred to for convenience as "CUVISI") is calculated and assigned. CUVISI is used as a basis for further calculations upon which the crude oil can be classified. API gravity and/or aromaticity are also calculated and assigned from the CUVISI. CUVISI or API gravity can be used to characterize the sample as extra heavy gravity, heavy gravity, medium gravity, light gravity, or super light gravity crude oil. Aromaticity, which is a measure of the percentage of the aromatic carbon atoms present in the sample, can also be used to characterize the crude oil sample. The correlations will provide for the necessary characterization of the nature of crude oils without fractionation/distillation typically required for the crude oil assays. The method and system will enable producers, marketers and refiners to benchmark the oil quality and valuate the oil without performing the customary extensive and time-consuming crude oil assays.

BRIEF DESCRIPTION OF THE DRAWING

Further advantages and features of the present invention will become apparent from the following detailed description of the invention when considered with reference to the accompanying drawings, in which.

DETAILED DESCRIPTION OF INVENTION

In the system and method herein, spectra are obtained by a suitable known or to be developed UV-visible spectrophotometry techniques UV-visible spectrophotometry is carried out on a sample of crude oil according to the method and system herein to provide unique information about aromatic and heteroaromatic compounds which absorb strongly in the UV region (200 nm-400 nm). Specific individual aromatic compounds and components have maxima at well-defined wavelengths. Wavelength maxima of known aromatic compounds and components are evaluated and extracted from the UV spectra of crude oils. These maxima are used to formulate indices for the aromatic content of the crude oil. These indices can be used to assign properties to the oil, e.g., API gravity, sulfur content, and other selected characteristics that define the quality and nature of the constituent products. According to the provided method and system, this information is obtained relatively rapidly and inexpensively from a UV-visible scan as compared to the conventional assay methods.

The system and method is applicable for naturally occurring hydrocarbons derived from crude oils, bitumens, heavy oils, shale oils and from refinery process units including hydrotreating, hydroprocessing, fluid catalytic cracking, coking, and visbreaking or coal liquefaction.

Figure 2:
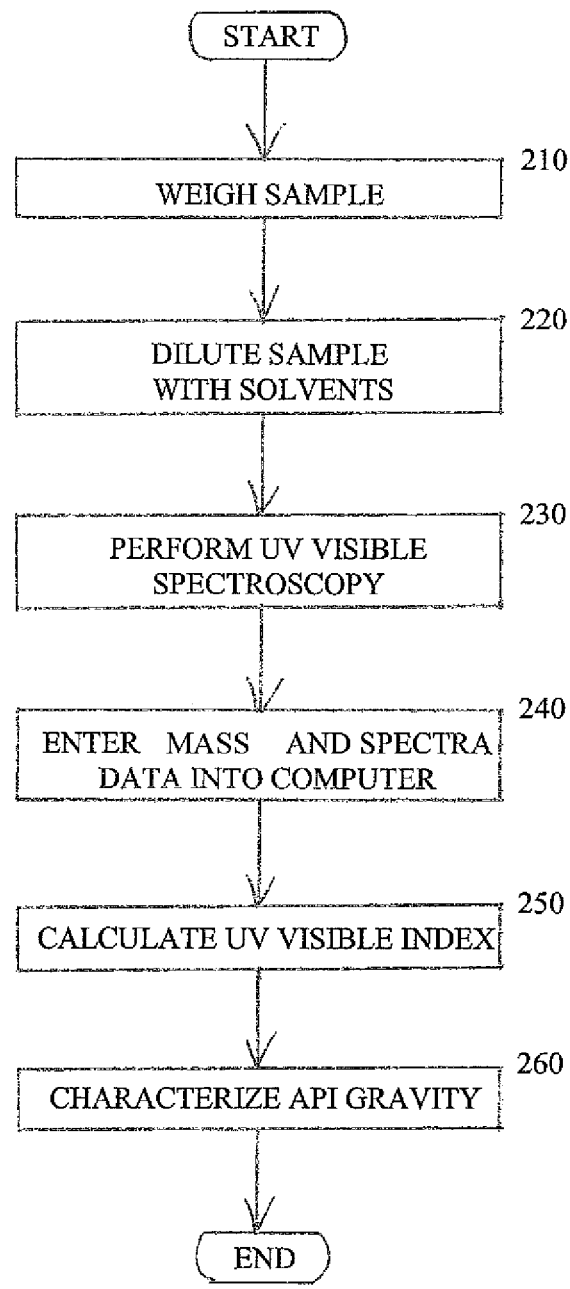
FIG. 2 is a process flow diagram of steps carried out to characterize the API gravity of a crude oil sample, using the system and method herein.

FIG. 2 shows a process flowchart in a method according to one embodiment herein. Crude oil samples were prepared and analyzed by ultraviolet visible spectrophotometry between 200-500 nm, in certain embodiments between 220-400 nm. In step 210, a crude oil sample is weighed.

In step 220, solutions are prepared by dissolving a sample of the crude oil in a two-part solvent system of a paraffinic solvent having from 5-20 carbon atoms and a polar solvent., e.g., at a ratio of 90:10% v/v. In certain embodiments, effective paraffinic solvents include iso-octane In certain embodiments, effective polar solvents include dichloromethane.

The use of a polar solvent prevents precipitation of asphaltenes from the crude oil sample and ensures that all solutions are translucent for the measurement. The polar solvents are selected based on their Hildebrand solubility factors or their two-dimensional solubility parameters. The overall Hildebrand solubility factor is a well known measure of polarity and has been calculated for numerous compounds. See, for example, the Journal of Paint Technology, Vol. 39, No. 505 (February 1967). The solvents can also be described by their two-dimensional solubility parameter. See, for example, I. A. Wiehe, "Polygon Mapping with Two-Dimensional Solubility Parameters", *I&EC Research*, 34, 661-673 (1995). The complexing solubility parameter component, which describes the hydrogen bonding and electron donor-acceptor interactions, measures the interaction energy that requires a specific orientation between an atom of one molecule and a second atom of a different molecule. The field force solubility parameter, which describes the van der Waals and dipole interactions, measures the interaction energy of the liquid that is not destroyed by changes in the orientation of the molecules.

The UV absorbance of the crude oil solutions is determined, for instance, in a conventional one cm quartz cell. The absorbance values of the samples are summed at predetermined increments (e.g., even numbers, odd number, or increments of any number) between a predetermined range, e.g., between 200-500 nm, in certain embodiments between 220-400 nm to calculate the characterization index.

In step 230, one or more samples of crude oil in dilute solution are analyzed by UV-visible spectrophotometry over the wavelengths 200-500 nm, in certain embodiments 220-400 nm.

In step 240, the mass and spectra data are entered into a computer. In step 250, the CUVISI is calculated.

Equation (1) shows a crude oil ultraviolet visible index, CUVISI.

$$CUVISI = \sum_{i=L}^{H} (Absorbance_{(Ni-220)}/x*10) \qquad (1)$$

where:

Absorbance=absorbance value of the prepared crude oil sample solution at a specific wavelength over the range L to H at intervals of N, whereby in certain embodiments L is between about 200 nm and 220 nm and H is between 400 nm and 500 nm, and N is between 1 and 3, and x is the weight of the sample used, in milligrams.

In one embodiment, in step 260 the sample is then characterized as follows:

For CUVISI≥115, the sample is extra heavy gravity crude oil;

For 100≤CUVISI<115, the sample is heavy gravity crude oil;

For 80≤CUVISI<100, the sample is medium gravity crude oil;

For 50≤CUVISI<80, the sample is light gravity crude oil; and

For CUVISI<50, the sample is super light gravity crude oil.

In another embodiment, in step 270 the API gravity of the sample is derived from the CUVISI, and the API gravity can also be used to characterize the sample. The API gravity value is calculated in step 280 as follows:

$$\text{API Gravity} = X1_{API}*CUVISI^2 X2_{API}*CUVISI + K_{API} \qquad (2)$$

where $X1_{API}$, $X2_{API}$ and $K_{API}$ are constants that are developed using linear regression techniques.

In certain embodiments, the sample can be characterized as follows:

For API Gravity≤20, the sample is extra heavy gravity crude oil;

For 20<API Gravity<27, the sample is heavy gravity crude oil;

For 27≤API Gravity<34, the sample is medium gravity crude oil;

For 34≤API Gravity<40, the sample is light gravity crude oil; and

For API Gravity≥40, the sample is super light gravity crude oil.

In another embodiment, the aromaticity of the sample can be derived from the CUVISI and used to further characterize the sample.

$$\text{Aromaticity} = X1_{AR}*CUVISI^2 + X2_{AR}*CUVISI + K_{AR} \qquad (3)$$

where $X1_{AR}$, $X2_{AR}$ and $K_{AR}$ are constants that are developed using linear regression techniques.

In certain embodiments, the sample can be characterized as follows:

For Aromaticity>10, the sample is aromatic;

For Aromaticity≤10, the sample is paraffinic/naphthenic.

Figure 3:
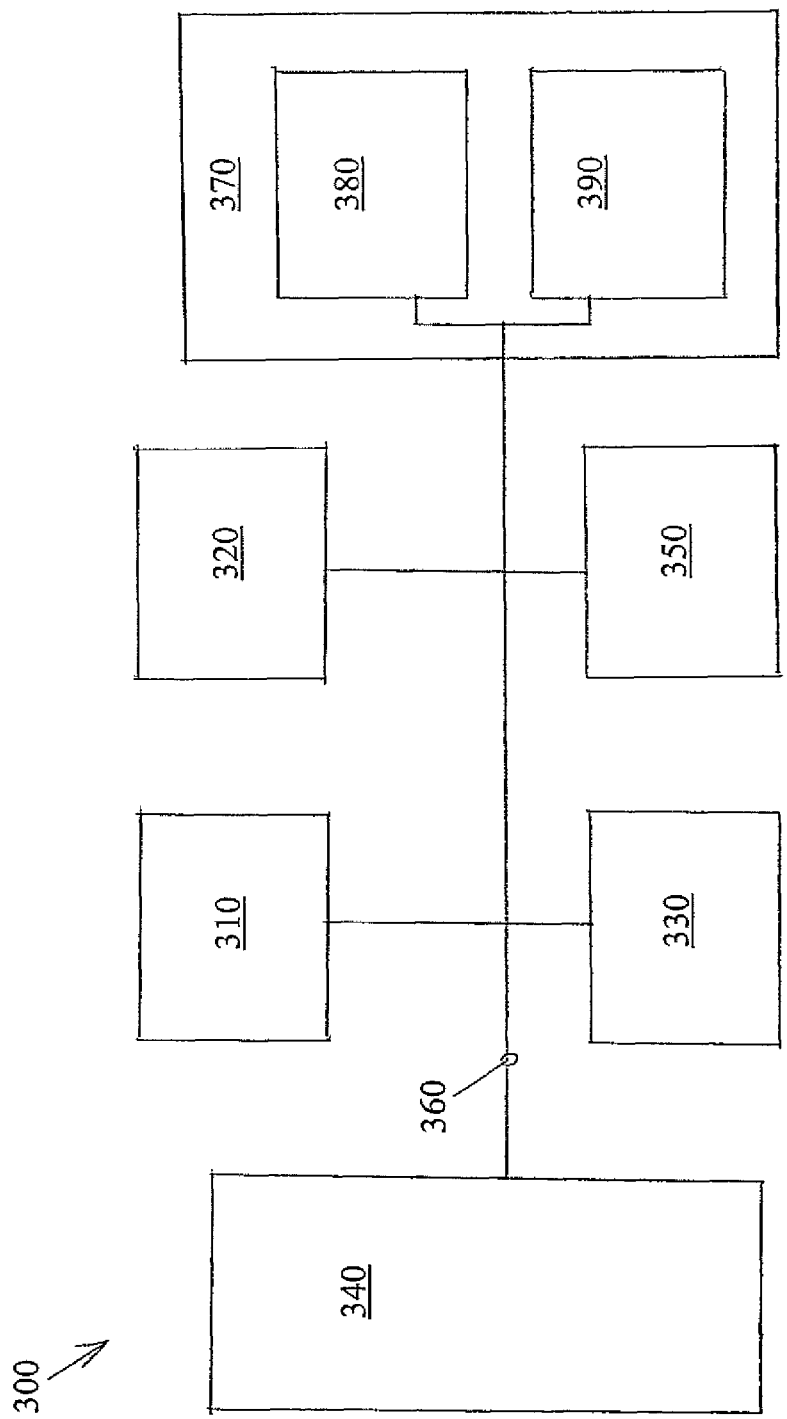
FIG. 3 is a block diagram of a component of a system for implementing the invention, according to one embodiment.

An exemplary block diagram of a computer system 300 by which indicative property calculation modules can be implemented is shown in FIG. 3. Computer system 300 includes a processor 310, such as a central processing unit, an input/output interface 320 and support circuitry 330. In certain embodiments, where the computer 300 requires direct human interaction, a display 340 and an input device 350 such as a keyboard, mouse or pointer are also provided. The display 340, input device 350, processor 310, input/output interface 320 and support circuitry 330 are shown connected to a bus 360 which also connects to a memory unit 370. Memory 370 includes program storage memory 380 and data storage memory 390. Note that while computer 300 is depicted with the direct human interface components of display 340 and input device 350, programming of modules and importation and exportation of data can also be accomplished over the interface 320, for instance, where the computer 300 is connected to a network and the programming and display operations occur on another associated computer, or via a detachable input device, as are well known in the art for interfacing programmable logic controllers.

Program storage memory 380 and data storage memory 390 can each comprise volatile (RAM) and non-volatile (ROM) memory units and can also comprise hard disk and backup storage capacity, and both program storage memory 380 and data storage memory 390 can be embodied in a single memory device or separated in plural memory devices. Program storage memory 380 stores software program modules and associated data, and in particular stores a crude oil UV visible index (CUVISI) calculation module and an API gravity characterization module that performs its calculations based upon the CUVISI. Data storage memory 390 stores data used and/or generated by the one or more modules of the present system, including mass of the oil sample, UV absorbance data or portions thereof used by the one or more modules of the present system, and calculated data generated by the one or more modules of the present system.

The calculated and assigned results in accordance with the systems and methods herein are displayed, audibly outputted, printed, and/or stored to memory for use as described herein.

It is to be appreciated that the computer system 300 can be any general or special purpose computer such as a personal computer, minicomputer, workstation, mainframe, a dedicated controller such as a programmable logic controller, or a combination thereof. While the computer system 300 is shown, for illustration purposes, as a single computer unit, the system can comprise a group/farm of computers which can be scaled depending on the processing load and database size, e.g., the total number of samples that are processed and results maintained on the system. The computer system 300 can serve as a common multi-tasking computer.

The computing device 300 preferably supports an operating system, for example, stored in program storage memory 390 and executed by the processor 310 from volatile memory. According to the present system and method, the operating system contains instructions for interfacing the device 300 to the calculation module(s). According to an embodiment of the invention, the operating system contains instructions for interfacing computer system 300 to the Internet and/or to private networks.

EXAMPLE

Crude oil samples were prepared and analyzed by ultraviolet visible spectrophotometry between 220-400 nm using a Jasco V-530 double beam spectrophotometer. The samples were weighed. Solutions were prepared by dissolving a milligram-sized sample of the crude oil in a two-part solvent system consisting of a paraffinic solvent having from 5-20 carbon atoms, preferred solvent being iso-octane, and a polar solvent, dichloromethane, at a ratio of 90:10% v/v. Dilute solutions were prepared by dissolving the oil in a two-part solvent system consisting of iso-octane (90 mL) and dichloromethane (10 mL). In a typical solution preparation, one drop (~6 mg±3 mg) of crude oil from a pre-weighed syringe is added to 100 mL of the solvent solution. The syringe is reweighed to determine the exact amount of the crude oil added. Each crude oil sample is analyzed at two concentration levels, e.g., 60 mg/L and 120 mg/L.

The UV absorbance of the crude oil solutions is determined in a conventional one cm quartz cell. Solutions are analyzed in 1 cm quartz cells using a Jasco V-530 double beam spectrophotometer over the wavelengths 220-400 nm. The absorbance values of the samples, normalized to 10 mg/L, are summed every even-numbered wavelength between 220 to 400 nm to calculate the characterization index.

The instrument is allowed to warm up for 30 minutes prior to analysis and is auto-zeroed without cells in both sample and reference beams. The reference cell is filled with the solvent mixture then placed in the reference beam. Solutions of the crude oil sample solutions prepared as described above are successively placed in a clean quartz sample cell and the spectra are recorded against the reference solvent blank. The spectra are recorded at a scan speed of 100 nm/min with a fast response time.

Figure 1:
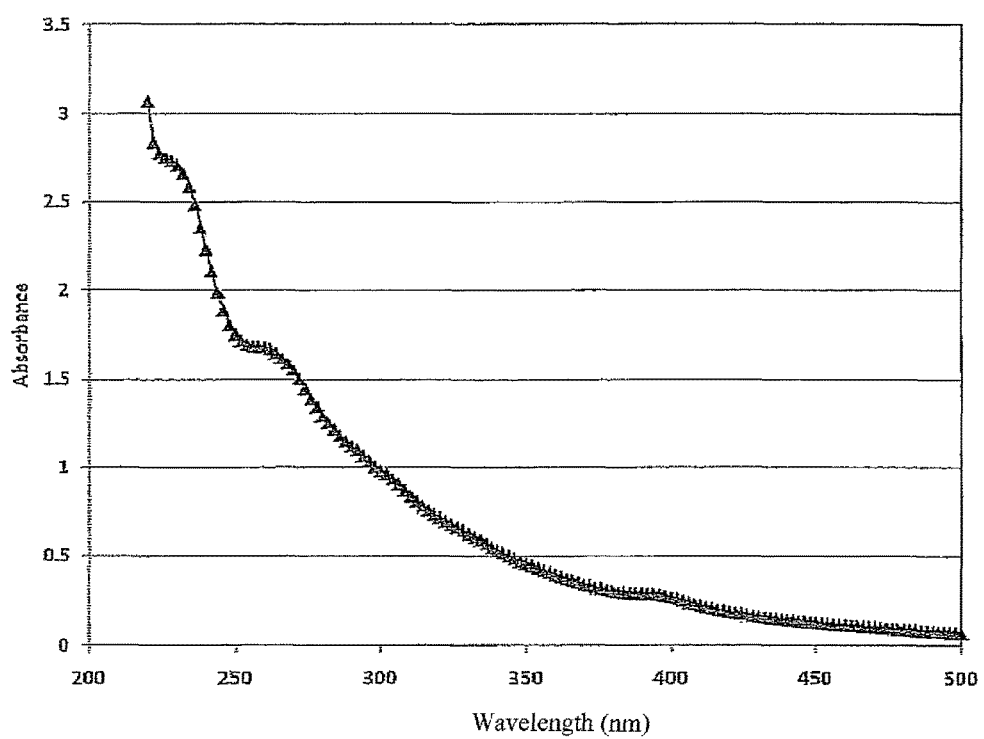
FIG. 1 is a graphic plot of typical ultraviolet visible spectroscopy data for a crude oil sample solution prepared as described herein.

Table 3 is an example of a tabulation of values for the sample of Arab heavy crude oil in the wavelength range 220-400 nm. This data is depicted in the curve of FIG. 1.

TABLE 3

Absorbances of Arab Heavy Crude Oils at Wavelength Ranging from 220-400 nm at 2 nm Interval

| Wave Length | Absor., nm |
|---|---|
| 220 | 3.076 |
| 222 | 2.841 |
| 224 | 2.778 |
| 226 | 2.753 |
| 228 | 2.735 |
| 230 | 2.708 |
| 232 | 2.663 |
| 234 | 2.591 |
| 236 | 2.486 |
| 238 | 2.361 |
| 240 | 2.236 |
| 242 | 2.113 |
| 244 | 1.994 |

TABLE 3-continued

Absorbances of Arab Heavy Crude Oils at Wavelength Ranging from 220-400 nm at 2 nm Interval

| Wave Length | Absor., nm |
|---|---|
| 246 | 1.891 |
| 248 | 1.811 |
| 250 | 1.755 |
| 252 | 1.719 |
| 254 | 1.698 |
| 256 | 1.689 |
| 258 | 1.688 |
| 260 | 1.685 |
| 262 | 1.673 |
| 264 | 1.649 |
| 266 | 1.621 |
| 268 | 1.59 |
| 270 | 1.552 |
| 272 | 1.502 |
| 274 | 1.447 |
| 276 | 1.39 |
| 278 | 1.341 |
| 280 | 1.297 |
| 282 | 1.255 |
| 284 | 1.218 |
| 286 | 1.183 |
| 288 | 1.15 |
| 290 | 1.121 |
| 292 | 1.096 |
| 294 | 1.067 |
| 296 | 1.036 |
| 298 | 1.006 |
| 300 | 0.981 |
| 302 | 0.962 |
| 304 | 0.935 |
| 306 | 0.905 |
| 308 | 0.871 |
| 310 | 0.839 |
| 312 | 0.809 |
| 314 | 0.783 |
| 316 | 0.758 |
| 318 | 0.735 |
| 320 | 0.714 |
| 322 | 0.696 |
| 324 | 0.678 |
| 326 | 0.662 |
| 328 | 0.645 |
| 330 | 0.627 |
| 332 | 0.609 |
| 334 | 0.59 |
| 336 | 0.57 |
| 338 | 0.551 |
| 340 | 0.532 |
| 342 | 0.518 |
| 344 | 0.502 |
| 346 | 0.486 |
| 348 | 0.472 |
| 350 | 0.458 |
| 352 | 0.445 |
| 354 | 0.432 |
| 356 | 0.418 |
| 358 | 0.406 |
| 360 | 0.394 |
| 362 | 0.382 |
| 364 | 0.37 |
| 366 | 0.359 |
| 368 | 0.349 |
| 370 | 0.34 |
| 372 | 0.332 |
| 374 | 0.323 |
| 376 | 0.316 |
| 378 | 0.309 |
| 380 | 0.303 |
| 382 | 0.299 |
| 384 | 0.294 |
| 386 | 0.292 |
| 388 | 0.29 |
| 390 | 0.289 |
| 392 | 0.288 |

TABLE 3-continued

Absorbances of Arab Heavy Crude Oils at
Wavelength Ranging from 220-400 nm at 2 nm Interval

| Wave Length | Absor., nm |
|---|---|
| 394 | 0.287 |
| 396 | 0.283 |
| 398 | 0.276 |
| 400 | 0.268 |

Equation (1) shows a crude oil ultraviolet visible index, CUVISI.

$$CUVISI = \sum_{i=220}^{400} (Absorbance_{(2i-220)}/x*10); \quad (1)$$

where:

Absorbance=absorbance value of the prepared crude oil sample solution at a specific wavelength over the range 220 nm to 400 nm at 2 nm intervals;

x=the weight of the sample used, in mg.

The data recorded in Table 3 produces a CUVISI of 98.697. This classifies this crude oil as medium gravity crude oil based on the characterizations above.

Exemplary constants for equations (2) and (3) are developed by linear regression, and are given as:

$X1_{API}$=−0.00176
$X2_{API}$=−0.00689
$K_{API}$=45.743
$X1_{AR}$=−0.0000309999
$X2_{AR}$=0.127188
$K_{AR}$=6.36006

Using these constants for the example provided in Table 3, for which CUVISI was determined to be 98.697:
The API Gravity is calculated as:
API Gravity=−0.00176*(98.697)$^2$−0.00689*(98.697)+ 45.743=27.9, which also identifies it as medium crude oil.
The Aromaticity value is calculated as:
Aromaticity=−0.0000309999*(98.697)$^2$+0.127188* (98.697)+6.36006=18.6, which identifies the sample as aromatic.

In alternate embodiments, the present invention can be implemented as a computer program product for use with a computerized computing system. Those skilled in the art will readily appreciate that programs defining the functions of the present invention can be written in any appropriate programming language and delivered to a computer in any form, including but not limited to: (a) information permanently stored on non-writeable storage media (e.g., read-only memory devices such as ROMs or CD-ROM disks); (b) information alterably stored on writeable storage media (e.g., floppy disks and hard drives); and/or (c) information conveyed to a computer through communication media, such as a local area network, a telephone network, or a public network such as the Internet. When carrying computer readable instructions that implement the present invention methods, such computer readable media represent alternate embodiments of the present invention.

As generally illustrated herein, the system embodiments can incorporate a variety of computer readable media that comprise a computer usable medium having computer readable code means embodied therein. One skilled in the art will recognize that the software associated with the various processes described can be embodied in a wide variety of computer accessible media from which the software is loaded and activated. Pursuant to In re Beauregard, 35 USPQ2d 1383 (U.S. Pat. No. 5,710,578), the present invention contemplates and includes this type of computer readable media within the scope of the invention. In certain embodiments, pursuant to In re Nuijten, 500 F.3d 1346 (Fed. Cir. 2007) (U.S. patent application Ser. No. 09/211,928), the scope of the present claims is limited to computer readable media, wherein the media is both tangible and non-transitory.

The system and method of the present invention have been described above and with reference to the attached figure; however, modifications will be apparent to those of ordinary skill in the art and the scope of protection for the invention is to be defined by the claims that follow.

We claim:

1. A system for characterizing an aromaticity value of an oil sample, wherein the oil sample is selected from naturally occurring hydrocarbons derived from crude oils, bitumens, heavy oils or shale oils, based upon ultraviolet visible spectroscopy data derived from the sample, the system comprising:
   a non-volatile memory device that stores calculation modules and data, the data including ultraviolet visible spectroscopy data indicative of absorbance values of the oil sample mixed with a solvent over a range of wavelengths;
   a processor coupled to the memory;
   a first calculation module that calculates and assigns an index value for the oil sample as a summation of the absorbance values of the oil sample mixed with solvent over the range of wavelengths, divided by the weight of the sample;
   and a second calculation module that calculates and assigns the aromaticity value gravity of the oil sample based upon the assigned index value.

2. The system of claim 1, further comprising a third calculation module that calculates and assigns an API gravity value to the oil sample based upon the index value.

3. The system of claim 2, wherein the first calculation module calculates and assigns the index value based on the ultraviolet visible spectroscopy data and a mass of the oil sample.

4. The system of claim 1, wherein the first calculation module calculates and assigns the index value based on the ultraviolet visible spectroscopy data and a mass of the oil sample.

5. The system as in claim 1, wherein the ultraviolet visible spectroscopy data is obtained by ultraviolet visible spectroscopy analysis is in a wavelength range from 220-500 nm.

6. The system of claim 5, wherein the ultraviolet visible spectroscopy data is obtained from an ultraviolet visible spectroscopy analysis in a wavelength range from 220-400 nm.

7. The system of claim 1, wherein the second calculation module calculates and assigns the aromaticity value of the oil sample with a polynomial equation with a set of predetermined constant coefficients developed using linear regression, and the assigned index value.

8. A system for characterizing an aromaticity value of an oil sample, wherein the oil sample is selected from naturally occurring hydrocarbons derived from crude oils, bitumens, heavy oils or shale oils, the system comprising:
   an ultraviolet visible spectrometer that outputs ultraviolet visible spectroscopy data derived from the oil sample mixed with a solvent, a non-volatile memory device that stores calculation modules and data, the data including outputted ultraviolet visible spectroscopy data indicative of absorbance values of the oil sample mixed with solvent over a range of wavelengths;

a processor coupled to the memory;

a first calculation module that calculates and assigns an index value for the oil sample as a summation of the absorbance values of the oil sample mixed with solvent over the range of wavelengths, divided by the weight of the sample;

and a second calculation module that calculates and assigns the aromaticity value of the oil sample based upon the assigned index value.

9. The system of claim 8, further comprising a third calculation module that calculates and assigns an API gravity value to the oil sample based upon the index value.

10. The system of claim 9, wherein the first calculation module calculates and assigns the index value based on the ultraviolet visible spectroscopy data and a mass of the oil sample.

11. The system of claim 8, wherein the first calculation module calculates and assigns the index value based on the ultraviolet visible spectroscopy data and a mass of the oil sample.

12. The system as in claim 8, wherein the ultraviolet visible spectroscopy data is obtained by ultraviolet visible spectroscopy analysis is in a wavelength range from 220-500 nm.

13. The system of claim 12, wherein the ultraviolet visible spectroscopy data is obtained from an ultraviolet visible spectroscopy analysis in a wavelength range from 220-400 nm.

14. The system of claim 8, wherein the second calculation module calculates and assigns the aromaticity value of the oil sample with a polynomial equation with a set of predetermined constant coefficients developed using linear regression, and the assigned index value.

15. A method for operating a computer to characterize an aromaticity value of an oil sample, wherein the oil sample is selected from naturally occurring hydrocarbons derived from crude oils, bitumens, heavy oils or shale oils, based upon ultraviolet visible spectroscopy data, the method comprising:

entering into the computer ultraviolet visible spectroscopy data indicative of absorbance values of the oil sample mixed with a solvent over a range of wavelengths;

calculating and assigning an index value of the oil sample as a summation of the absorbance values of the oil sample mixed with solvent over the range of wavelengths, divided by the weight of the sample; and calculating and assigning the aromaticity value of the sample from the assigned index value.

16. The method of claim 15, further comprising calculating and assigning an API gravity value.

17. The method of claim 16, further comprising weighing the sample to obtain a mass, and wherein calculating and assigning the index value is based on the ultraviolet visible spectroscopy data and the mass of the oil sample.

18. The method of claim 15, further comprising weighing the sample to obtain a mass, and wherein calculating and assigning the index value is based on the ultraviolet visible spectroscopy data and the mass of the oil sample.

19. The method as in claim 15, wherein the ultraviolet visible spectroscopy data is obtained by ultraviolet visible spectroscopy analysis is in a wavelength range from 220-500 nm.

20. The method of claim 19, wherein the ultraviolet visible spectroscopy data is obtained from an ultraviolet visible spectroscopy analysis in a wavelength range from 220-400 nm.

21. The method of claim 15, wherein the aromaticity value of the oil sample is calculated with a polynomial equation with a set of predetermined constant coefficients developed using linear regression, and the assigned index value.

22. A method for operating a computer to characterize an aromaticity value of an oil sample, wherein the oil sample is selected from naturally occurring hydrocarbons derived from crude oils, bitumens, heavy oils or shale oils, the method comprising:

operating an ultraviolet visible spectrometer that to obtain ultraviolet visible spectroscopy data derived from the oil sample mixed with a solvent;

entering into the computer the ultraviolet visible spectroscopy data, the data indicative of absorbance values of the oil sample mixed with solvent over a range of wavelengths;

calculating and assigning an index value of the oil sample based upon ultraviolet visible spectroscopy data; and calculating and assigning an index value of the oil sample as a summation of the absorbance values of the oil sample mixed with solvent over the range of wavelengths, divided by the weight of the sample; and calculating and assigning the aromaticity value to the sample from the assigned index value.

23. The method of claim 22, further comprising calculating and assigning an API gravity value.

24. The method of claim 23, further comprising weighing the sample to obtain a mass, and wherein calculating and assigning the index value is based on the ultraviolet visible spectroscopy data and the mass of the oil sample.

25. The method of claim 22, further comprising weighing the sample to obtain a mass, and wherein calculating and assigning the index value is based on the ultraviolet visible spectroscopy data and the mass of the oil sample.

26. The method as in claim 22, wherein the ultraviolet visible spectroscopy data is obtained by ultraviolet visible spectroscopy analysis is in a wavelength range from 220-500 nm.

27. The method of claim 26, wherein the ultraviolet visible spectroscopy data is obtained from an ultraviolet visible spectroscopy analysis in a wavelength range from 220-400 nm.

28. The method of claim 22, further comprising preparing the sample for ultraviolet visible spectroscopy analysis by diluting the sample with solvent.

29. The method of claim 28, wherein the solvent used is a mixture of paraffinic and polar solvents.

30. The method of claim 29, wherein the paraffinic solvent contains carbon from 5-20 atoms.

31. The method of claim 29, wherein the polar solvent is selected based on its Hildebrand solubility factor or by its two-dimensional solubility parameter.

32. The method of claim 31, wherein the polar solvent has a Hildebrand solubility rating of at least 19.

33. The method of claim 31, wherein the two-dimensional solubility factors of the polar solvent are the complexing solubility parameter and the field force solubility parameter.

34. The method of claim 33, wherein the polar solvent's complexing solubility parameter component describes the hydrogen bonding and electron donor acceptor interactions.

35. The method of claim 33, wherein the polar solvent's field force solubility parameter is based on the van der Waals and dipole interactions.

36. The method of claim 29, wherein the paraffinic-to-polar solvent ratio is 70:30 or greater.

37. The method of claim 29, wherein the paraffinic-to-polar solvent ratio is 90:10 or greater.

38. The method of claim 22, wherein the aromaticity value of the oil sample is calculated with a polynomial equation with a set of predetermined constant coefficients developed using linear regression, and the assigned index value.

39. A method for operating a computer to characterize an aromaticity value of an oil sample comprising:
preparing the oil sample for ultraviolet visible spectroscopy analysis by diluting the sample with solvent, wherein the solvent used is a mixture of paraffinic and polar solvents, and wherein the polar solvent is selected based on its Hildebrand solubility factor or by its two-dimensional solubility parameter;
operating an ultraviolet visible spectrometer that to obtain ultraviolet visible spectroscopy data derived from the oil sample;
entering into the computer the ultraviolet visible spectroscopy data, the data indicative of absorbance values over a range of wavelengths;
calculating and assigning an index value of the oil sample based upon ultraviolet visible spectroscopy data; and
calculating and assigning the aromaticity value to the sample from the assigned index value.

40. The method of claim 39, further comprising calculating and assigning an API gravity value.

41. The method of claim 40, further comprising weighing the sample to obtain a mass, and wherein calculating and assigning the index value is based on the ultraviolet visible spectroscopy data and the mass of the oil sample.

42. The method of claim 39, further comprising weighing the sample to obtain a mass, and wherein calculating and assigning the index value is based on the ultraviolet visible spectroscopy data and the mass of the oil sample.

43. The method of claim 39, wherein the ultraviolet visible spectroscopy data is obtained by ultraviolet visible spectroscopy analysis is in a wavelength range from 220-500 nm.

44. The method of claim 43, wherein the ultraviolet visible spectroscopy data is obtained from an ultraviolet visible spectroscopy analysis in a wavelength range from 220-400 nm.

45. The method of claim 39, wherein the paraffinic solvent contains carbon from 5-20 atoms.

46. The method of claim 39, wherein the polar solvent has a Hildebrand solubility rating of at least 19.

47. The method of claim 39, wherein the two-dimensional solubility factors of the polar solvent are the complexing solubility parameter and the field force solubility parameter.

48. The method of claim 47, wherein the polar solvent's complexing solubility parameter component describes the hydrogen bonding and electron donor acceptor interactions.

49. The method of claim 47, wherein the polar solvent's field force solubility parameter is based on the van der Waals and dipole interactions.

50. The method of claim 39, wherein the paraffinic-to-polar solvent ratio is 70:30 or greater.

51. The method of claim 39, wherein the paraffinic-to-polar solvent ratio is 90:10 or greater.

52. The method of claim 39, further comprising weighing the sample to obtain a mass, and wherein calculating and assigning the index value is with a summation of the absorbance values of the oil sample mixed with solvent over the range of wavelengths, divided by the weight of the sample.

53. The method of claim 52, wherein the aromaticity value of the oil sample is calculated with a polynomial equation with a set of predetermined constant coefficients developed using linear regression, and the assigned index value.

* * * * *